United States Patent [19]
Bellande et al.

[11] Patent Number: 6,071,492
[45] Date of Patent: Jun. 6, 2000

[54] CARDIAC TROPISM RADIOPHARMACEUTICAL PRODUCTS INCORPORATING A NITRIDE COMPLEX OF A TRANSITION METAL AND HAVING A RAPID MYOCARDIAL CLEARANCE

[75] Inventors: Emmanuel Bellande, Saulx les Chartreux; Jacques Laine, Orsay; Véronique Comazzi, Vanves; Roberto Pasqualini, Clamart, all of France

[73] Assignee: CIS bio International, Gif sur Yvette, France

[21] Appl. No.: 08/981,831

[22] PCT Filed: Jul. 16, 1996

[86] PCT No.: PCT/FR96/01103

§ 371 Date: Jan. 16, 1998

§ 102(e) Date: Jan. 16, 1998

[87] PCT Pub. No.: WO97/03705

PCT Pub. Date: Feb. 6, 1997

[30]    Foreign Application Priority Data

Jul. 17, 1995 [FR] France ............... 95 08606

[51] Int. Cl.⁷ ............... A61K 51/08; C07F 5/00
[52] U.S. Cl. ............... 424/1.65; 534/10; 534/14
[58] Field of Search ............... 424/1.65, 1.69, 424/1.53; 534/10, 14

[56]    References Cited

U.S. PATENT DOCUMENTS 5,288,476  2/1994  Pasqualini et al. ............... 424/1.65
5,399,339  3/1995  Pasqualini et al. ............... 424/1.53

*Primary Examiner*—Jose' G. Dees
*Assistant Examiner*—Michael G. Hartley
*Attorney, Agent, or Firm*—Oblon, Spivak, McClelland, Maier & Neustadt, P.C.

[57]    ABSTRACT

The present invention relates to cardiac tropism radiopharmaceutical products incorporating a nitride complex os a transition metal and having a rapid myocardial clearance.

These complexes are based on the formula:

$$(M\equiv N)L^1L^2 \qquad (I)$$

in which M is a transition metal such as $^{99m}$Tc and $L^1$ and $L^2$ comply with the formula:

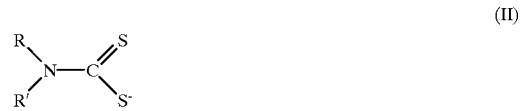

(II)

in which at least one of the R and R' represents a branched alkyl group having one or more ether functions, a tetrahydrofurfuryl or ether group, a tetrahydrofurfuryl or dioxaspiro or dialkoxy piperidino groups.

22 Claims, No Drawings

CARDIAC TROPISM RADIOPHARMACEUTICAL PRODUCTS INCORPORATING A NITRIDE COMPLEX OF A TRANSITION METAL AND HAVING A RAPID MYOCARDIAL CLEARANCE

This application is a 371 of PCT/FR96/01103, filed Jul. 16, 1996.

BACKGROUND OF THE INVENTION

The present invention relates to a cardiac tropism radiopharmaceutical product incorporating a nitride complex of a transition metal M having a central part M≡N usable for myocardial scintigraphy.

According to the invention, the term transition metal is understood to mean a metal, whose layer d is partly filled in the usual degree of oxidation of said metal. It applies to elements of periods III to XII of the periodic table of elements having eighteen columns. Examples of such metals are Tc, Ru, Co, Pt, Fe, Os, Ir, W, Re, Cr, Mo, Mn, Ni, Rh, Pd, Nb and Ta.

Technetium nitride complexes have been described by J. Baldas et al. in the following documents: international patent application WO-85/03063, J. Chem. Soc. Dalton Trans., 1981, pp 1796–1801 and the book "Technetium in Chemistry and Nuclear Medicine", Ed. M. Nicolini, G. Bandoli, U. Mazzi, Cortine Int. Verone, 1986, pp 103 to 108.

DESCRIPTION OF THE BACKGROUND

Technetium nitride complexes having a cardiac tropism have been described in WO-A-90/06137. These complexes have a central portion M≡N and ligands of the dithiocarbamate type having side groups of the alkyl type, optionally substituted by alkoxy, alkylcarboxy, carbamoyl or amino groups.

These complexes have good biological properties with respect to their cardiac retention, but can have a disturbing, early pulmonary fixation for myocardial examinations and they are relatively slowly eliminated from the organism, particularly the heart.

This is a disadvantage for the scintigraphic examination of the myocardiuim. Thus, a complete examination of the myocardium generally requires two injections of the radiopharmaceutical product, one at rest and the other after an effort test. With radiopharmaceutical products having a stable fixation in the myocardium, these four injections must be spaced by a minimum of 4 hours in order to eliminate the residual cardiac activity due to the first injection. It would therefore be of significant interest to have more rapidly eliminated, cardiac tropism radiopharmaceutical products.

Another problem encountered with radiopharmaceutical products of this type is their hepatic fixation, which can be prejudicial if it is of a persistent nature. Thus, such a fixation does not make it possible to carry out a satisfactory scintigraphic examination of the myocardium, when the second injection is too close to the first. It would therefore be of interest to have cardiac tropism radiopharmaceutical products which are rapidly eliminated from the liver and heart.

SUMMARY OF THE INVENTION

The present invention relates to radiopharmaceutical products incorporating a transition metal nitride complex, which are more rapidly eliminated from the heart and which do not have disturbing pulmonary and hepatic fixations. These complexes also comprise ligands of the dithiocarbamate type, but the alkyl groups of these ligands are either a branched chain having at least one ether function, or a branched chain, whereof a carbon atom is substituted by two alkoxy groups, which corresponds to an acetyl function.

According to the invention, the radiopharmaceutial product comprises a complex of a transition metal complying with the formula:

(M≡N)L$^1$L$^2$     (I)

in which M is a transition metal, and L$^1$ and L$^2$, which can be the same or different, comply with the formula:

(II)

in which R and R', which are the same or different, represent:

an alkyl group, a group of formula:

(III)

in which:

R$^1$ is an alkyl group, R$^2$ is an alkyl group or an alkoxy group, or R$^1$ and R$^2$ form together the group —CH$_2$CH$_2$O—, R$^1$ is an alkyl group, R$^2$ is an alkyl group or an alkoxy group, or R$^1$ and R$^2$ form together the group —CH$_2$CH$_2$O—, R$^3$ is a hydrogen atom or an alkyl group and n is equal to 0, 1, 2 or 3, a group of formula:

(IV)

in which R$^1$ and R$^3$ are as defined hereinbefore and R$^4$ is an alkyl group, the group of formula:

(V)

a group of formula:

R$^1$O(CH$_2$CH$_2$O)$_p$CH$_2$CH$_2$—     (VI)

in which R$^1$ is as defined hereinbefore and p is equal to 1 or 2, or in which R and R' together with the nitrogen atom to which they are linked, form the group of formula:

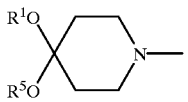

(VII)

in which $R^1$ and $R^5$ are identical or different alkyl groups, or in which $R^1$ and $R^5$ form together —CH$_2$—CH$_2$—, provided that both R and R' do not represent an alkyl group.

DETAILED DESCRIPTION OF THE INVENTION

The ligands $L^1$ and $L^2$ of the transition metal complex according to the invention thus incorporate a branched alkyl group of formula (III) or formula (V), a tetrahydrofurfuryl group, a straight polyether-type group, or a dioxaspiro or dialkoxy piperdino-type group, which gives them better clearance properties.

In the complexes of the invention, the transition metal M is in particular chosen as a function of the application of the radiopharmaceutical product.

Thus, when it is wished to use the product for diagnosis, use is made of a radioactive transition metal having a relatively short period. e.g. technetium$^{99m}$.

In the case where it is wished to use the radiopharmaceutical product for therapy, use is made of a transition metal emitting an effective radiation for the therapy and having a longer life, such as rhenium, e.g. Re-186 or Re-188.

In the formula given hereinbefore for R and R', the alkyl groups represented by $R^1$, $R^2$, $R^3$, $R^4$ and $R^5$ can be straight or branched. In general, use is made of alkyl groups having 1 to 5 carbon atoms, particularly ethyl and methyl groups.

The alkyl group used for R or R' can also be straight or branched and preferably have 1 to 5 carbon atoms.

When $R^2$ represents an alkyl group, it can also be a straight or branched group and preferably said alkoxy group has 1 to 5 carbon atoms.

In the transition metal complex according to the invention, the ligands $L^1$ and $L^2$ can be the same or different and are preferably the same.

According to a first embodiment of the invention, at least one of the $L^1$ and $L^2$ complies with the formula (II) in which:

R and/or R' represent an acetal group of formula:

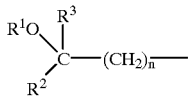

(III)

in which $R^1$ represents an alkyl group, e.g. the ethyl or methyl group, $R^2$ represents an alkoxy group, e.g. the ethoxy or methoxy group, $R^1$ represents a hydrogen atom or an alkyl group, e.g. the methyl group, and n is equal to 0, 1, 2 or 3.

According to a second embodiment of the invention, at least one of the ligands $L^1$ and $L^2$ complies with formula (II) in which R and/or R' represent a group of formula:

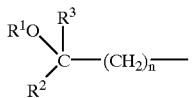

(III)

in which $R^1$, $R^2$ and $R^3$ are identical or different alkyl groups, e.g. the methyl group.

According to a third embodiment of the invention, at least one of the ligands $L^1$ and $L^2$ complies with the formula (II) in which:

R and/or R' comply with the formula (IV):

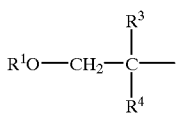

(IV)

in which $R^1$ represents an alkyl group, e.g. the methyl group, $R^3$ represents a hydrogen atom and $R^4$ represents an alkyl group, such as the ethyl or methyl group.

According to a fourth embodiment of the invention, at least one of the $L^1$ and $L^2$ complies with the formula (II) in which:

R and/or R' represent the group of formula:

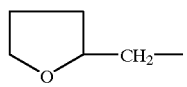

(V)

The technetium nitride complexes used in the invention can be prepared by conventional processes, e.g. by the Baldas process. However, they are preferably prepared by simpler processes, which can be more easily carried out in a hospital and which lead to high yields, e.g. the processes described in WO-A-93/01839, WO-A-92/00982 and WO-A-90/6137.

Preferably, according to the invention use is made of the process described in WO92/00982 consisting of reacting in solution an oxygen compound of the transition metal M, with 1) a nitrogen ligand constituted either by a pharmaceutically acceptable metal or ammonium nitride, or by a nitrogen compound having a N—N unit, in which the N's are connected to hydrogen atoms and/or monovalent organic groups, e.g. via a carbon atom or a S atom, or in which one of the N's is connected to the carbon atom of a divalent organic group via a double bond and the other N is connected to hydrogen atoms and/or monovalent organic groups, e.g. via a carbon atom;

2) a reducing agent constituted either by a pharmaceutically acceptable metal or ammonium dithionite, or by the tin II present in ionic form in the solution; and 3) a compound complying with the formula:

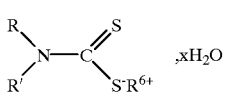

(VIII)

in which R and R' have the meanings given hereinbefore, $R^6$ is an alkali metal ion, H$^+$ and NH$_4^+$, and x is equal to 0 or an integer from 1 to 5.

This reaction between the oxygen compound of the transition metal, the reducing agent, the nitrogen ligand and the compound of formula (VIII) can be performed in one or two stages.

Working preferably takes place in two stages. Thus, in a first stage the oxygen compound of the transition metal is reacted with the nitrogen ligand and the reducing agent, and in a second stage the product obtained at the end of the first stage is reacted with the compound of formula (VIII).

When tin (II) is used as the reducing agent, it can be introduced into the solution from one or more reagents able to keep it in ionic form in the presence of the nitrogen ligand and the compound of formula (VIII).

The tin can in particular be introduced in the form of the tin (II) salt, e.g. stannous chloride dihydrate. In order to keep it in ionic form in the solution, simultaneous addition takes place of a complexing agent having a complexing power with respect to the tin which is stronger than those of the nitrogen ligand and the compound of formula (VIII). The complexing agent can in particular be 1,2-diamino-propane-N,N,N',N'-tetraacetic acid or a salt thereof.

Preferably, according to the invention, stannous chloride dihydrate is used as the reducing agent and succinyl dihydrazide as the nitrogen ligand.

The compounds of formula (VIII) used for the preparation of the radio-pharmaceutical products according to the invention can be prepared by conventional processes from the corresponding amines of formula:

(IX)

in which R and R' are as defined hereinbefore, by reacting these amines with carbon disulphide in the presence of soda.

The secondary amines of formula (IX) can be prepared by reacting a primary amine of formula:

with a halogen of formula R'X, in which X is a halogen, preferably Br.

The radiopharmaceutical product according to the invention is generally prepared at the time of use. The invention also relates to a kit for the preparation of a cardiac tropism radiopharmaceutical product comprising:

a first bottle containing a tin salt and a complexing agent able to maintain the tin in ionic form, a second bottle containing the nitrogen ligand and a third bottle containing a compound complying with formula (VIII).

According to a variant, the kit only has two bottles:

a first bottle containing the tin salt, the complexing agent for keeping the tin in ionic form and the nitrogen ligand and a second bottle containing the compound of formula (VIII).

Advantageously, the compound of formula (VIII) is chosen from among sodium-(N-ethyl, N-(R,S)-2-methoxyisopropyl) dithiocarbamate, sodium-(N-ethyl, N-(R)-2-methoxyisopropyl)-dithiocarbamate, sodium-(N-ethyl, N-(S)-2-methoxyisopropyl)-dithiocarbamate, sodium-[N,N-bis(2,2-dimethoxyethyl)]-dithiocarbaniate, sodium-[N-(2,2-dimethoxyethyl), N-(3,3-dimethoxypropyl)]-dithiocarbamate, sodium-[N-(2,2-dimethoxyethyl), N-ethyl)]-dithiocarbamate.

The products present in each bottle can be in the form of a solution or in lyophiliazed form.

With this kit, it is possible to directly prepare the desired radio-pharmaceutical product in a nuclear medicine hospital department, by adding to the content of the first bottle a solution of the oxygen compound of the transition metal, e.g. an ammonium or alkali metal pertechnetate solution, then by adding to the thus obtained product the content of the second bottle.

In view of the fact that the products are intended for an intravenous injection to living beings, appropriate production and preparation conditions must be used in order to obtain appropriately sterile and apyrogenic solutions.

In order to prepare the solutions, it is possible to use sterile, apyrogenic water or sterile, apyrogenic, alcoholic or hydroalcoholic solutions, and carry out a storage of the solutions under nitrogen.

For preparing lyophilized compositions, solutions obtained under the same conditions as hereinbefore are lyophilized in conventional equipment.

The radiopharmaceutical products according to the invention can in particular be used for scintigraphy of the myocardium.

In this case, following the preparation of the technetium nitride complex, the latter is injected into the patient to be examined, which is followed by a scintigraphic examination of the heart.

For the injection of the product, the quantities of the different ligands are such that they substantially correspond to the stoichiometry of the complexes to be obtained. The final quantity injected more particularly depends on the ligands used and their toxicity. In general, satisfactory results are obtained by using total ligand quantities ranging from 0.05 to 0.40 mg/kg of body weight.

The total dose of transition metal, e.g. technetium, is generally in the range 185 to 740 Mbq (5 to 20 millicuries).

With the administration of the transition metal nitride complex, it is possible to carry out a satisfactory examination in a very short time, e.g. 2 to 5 minutes after the injection and a good contrast, clear images and a good detection of lesions are obtained.

Moreover, with these compounds it is possible to carry out two successive examinations in a very brief period, e.g. performing the second injection one hour after the first, due to the rapid clearance of the radiopharmaceutical products.

Thus, the radiopharmaceutical products according to the invention, particularly those in which the ligands have a branched R or R' group with an alkoxy substituent complying to formula (III), with $R^2$ and $R^3$ being alkyl groups and with $R^2$ being an alkoxy group and $R^3$ a hydrogen atom, have the advantage of being eliminated from the liver by the gall duct and of thus concentrating the residual activity in the gall bladder. Thus, even when the second injection takes place one hour after the first, no disturbance is caused by the residual hepatic activity due to the first injection, because said residual activity is in the gall bladder, namely in an area which does not interfere with the heart examination.

The situation would not be the same on using radiopharmaceutical products like those of the prior art, in which the ligands have a group R of the straight alkoxy or alkoxyalkyl type, like the compounds of examples 11 and 17 of the aforementioned WO-A-90/06137.

Thus, in the case of these compounds where the R groups of the ligands $L^1$ and $L^2$ respectively correspond to the formulas:

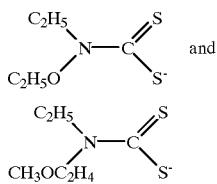

The residual hepatic fixation relates to all the liver one hour after the injection, because there is no activity concentration in the gall bladder.

Other features and advantages of the invention can be better gathered from studying the following examples given in an illustrative and non-limitative manner.

EXAMPLE 1

Preparation of the nitride-bis[N-ethyl,N-(R,S,2-methoxyisopropyl)-dithiocarbamate]$^{99m}$Tc(V) complex 1) Preparation of the sodium-(N-ethyl,N-(R,S)-2-methoxyisopropyl)dithiocarbamate.

a) Preparation of the (N-ethyl,N-(R,S)-2-methoxyisopropyl)-amine.

0.1 mole of (R,S)-2-methoxyisopropyl-amine (Aldrich) is dissolved in 100 ml of water containing 0.2 mole of NaOH. In dropwise manner 0.1 mole of bromethane is added. The solution is refluxed for one night. The aqueous phase is extracted by 200 ml of diethyl ether. The organic phase is washed three times with 20 ml of 1N NaOH in water, in order eliminate the primary amine which has not reacted. The organic phase is dried on sodium sulphate and the secondary amine is distilled $TE_b=121°$ C. under 760 mm Hg.

b) Preparation of sodium-(N-ethyl,N-(R,S)-2-methoxyisopropyl)dithiocarbamate 0.05 mole of the amine prepared in a) is dissolved in 200 ml of ether containing 0.1 mole of NaOH in pellet form. Dropwise addition takes place of 0.1 mole of $CS_2$ and reaction is allowed to take place for 4 hours at ambient temperature. The organic phase is filtered and 500 ml of n-heptane are added. It is allowed to recrystallize for one night at 4° C., giving a white solid (sodium dithiocarbanate given as titer), which is recrystallized in an ether-n-heptane mixture.

NMR analysis in deuterium dimethyl sulphoxide (DMSO-D6).:

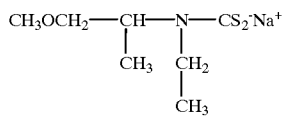

$\underline{CH_3}$O: singlet 3.35 ppm
$CH_3$O—$\underline{CH_2}$: doublet 4.05 ppm
—CH: quintuplet 6.3 ppm
$\underline{CH_3}$—CH: doublet 0.9 ppm
$\underline{CH_3}$—$CH_2$—N: triplet 1.1 ppm
$CH_3$—$\underline{CH_2}$—N quadruplet 3.65 ppm.

2) Preparation of the intermediate (Tc≡N)$^{2+}$

Addition takes place of 0.5 to 5 ml of a sodium pertechnetate solution ($^{99m}TcO_4^-$), 37 KBQ to 3.7 GBQ, to a penicillin-type bottle containing in lyophilized form:

20 μg of $SnCl_2$, $2H_2O$ (stannous chloride dihydrate), 10 mg of succinyl dihydrazide (SDH), 5 mg of 1,2-diaminopropane-N-N,N',N'-tetraacetic acid, 10 mg of γ-cyclodextrin.

0.05 mmole of phosphate buffer at pH=7.80.

The reaction is allowed to carry on for 10 minutes at ambient temperature, giving the intermediate (Tc≡N)$^{2+}$ 3) Preparation of the final complex Addition takes place of 1 ml of a sodium-(N-ethyl, N-(R,S)-2-methoxyisopropyl)-dithiocarbamate solution, as prepared in 1), to 10 mg/ml in water to the bottle containing the intermediate (Tc≡N)$^{2+}$. Reaction takes place for 5 minutes at ambient temperature and the final complex is obtained.

Radiochemical purity is tested by carrying out reverse phase, thin film chromatography (Whatman KC16F, eluent 30% methanol, 30% acetonitrile, 20% THF, 0.5 M $AcNH_4$ in 20% $H_2O$). The radiopharmaceutical obtained has a Rf=0.52. The radiochemical purity is equal to or higher than 96%.

EXAMPLE 2

Preparation of the nitride-bis [(N-ethyl Ne(R)-2-methoxyisopropyl)-dithiocarbamate]$^{99m}$Tc(V) complex 1) Synthesis of the ligand sodium-(N-ethyl, N-(R)-2-methoxyisopropyl)dithiocarbamate Firstly, the R-1-methoxyisopropyl amine is prepared in the following way.

0.2 mole of R-2-amino-1-propanol (Aldrich) is dissolved in 200 ml of anhydrous ether under a nitrogen atmosphere. Addition takes place of 0.25 mole of metallic sodium (Na). Refluxing takes place for 6 hours. This is followed by the dropwise addition of 0.2 mole of methyl iodide. The solution is filtered, the filtrate dried on sodium sulphate and the amine is distilled, $TE_b=93°$ C. at atmospheric pressure.

This is followed by the preparation of the substituted amine and then the corresponding sodium dithiocarbamate following the same operating procedure as in example 1, stages 1a) and 1b).

This gives the ligand sodium-N-ethyl, N-(2(R)-methoxyisopropyl)-dithiocarbamate. NMR analysis of this product in DMSO leads to a spectrum identical to that obtained in example 1.

2) Preparation of the intermediate (Tc≡N)$^{2+}$

The latter is prepared following the same operating procedure as in example 1, but using sodium dithiocarbamate prepared in the preceding stage.

3) Preparation of the final complex

The latter is prepared as in example 1 from the previously obtained intermediate. It has the following characteristics:

Rf=0.52 radiochemical purity≧97%.

EXAMPLES 3 TO 6

The same operating procedure as in examples 1 and 2 is followed for preparing the technetium complexes given in table 1, the characteristics of these complexes also being given in table 1.

EXAMPLE 7

Preparation of the nitride-bis-[N-ethyl, N-(R,S)-2-methoxypropyl)-dithiocarbamate]$^{99m}$Tc(V) complex.

Preparation firstly takes place of the ligand sodium-N-ethyl, N-(R,S-2-methoxypropyl)-dithiocarbamate working in the following way.

a) Preparation of R,S-2-methoxypropyl amine 0.2 mole of (R,S)-1-amino-2-propanol (Aldrich) is dissolved in 200 ml of anhydrous ether under a nitrogen atmosphere. 0.25 mole of metallic sodium is added. Refluxing takes place for 6 hours. This is followed by the dropwise addition of 0.2 mole of methyl iodide. The solution is filtered, the filtrate dried on sodium sulphate and the amine distilled. $TE_b=106°$ C. under 760 mmHg.

b) Preparation of the ligand

The procedure of example 1 is then adopted for preparing the ligand from said amine.

The same operating procedure as in example 1 is then used for preparing the technetium complex starting with said ligand. The characteristics of this complex are given in table 1.

EXAMPLE 8

The same operating procedure as in example 1 is followed for preparing the technetium complex according to table 1 from R,S-1-(methoxymethyl)-propyl amine prepared in the following way.

0.2 mole of (R,S)-2-amino-1-butanol (Aldrich) is prepared in 200 ml of anhydrous ether under a nitrogen atmosphere, followed by the addition of 0.25 mole of metallic sodium. Refluxing takes place for 6 hours, followed by the dropwise addition of 0.2 mole of methyl iodide. The solution is filtered, the filtrate dried on sodium sulphate and the amine is distilled, $TE_b=102°$ C. under 760 nm Hg.

The characteristics of the complex obtained are given in table 1.

EXAMPLE 9

The same operating procedure as in the preceding examples is followed for preparing the technetium complex according to table 1, using 2-methoxyisobutyl amine prepared in the following way.

0.3 mole of 2-2-dimethyl aziridine is dissolved in 80 ml of methanol containing 0.35 mole of methanol trifluoroborane complex. Reaction is allowed to take place for 7 days at ambient temperature and 0.45 mole of sodium methylate is added. The solution is filtered and distilled. The two amines obtained are separated:

2-methoxyisobutyl amine, $TE_b=126°$ C. under 760 mm Hg, 2-methoxy tert-butyl amine, $TE_b=103°$ C. under 760 mm Hg The characteristics of the complex obtained are given in table 1.

EXAMPLE 10

The operating procedure of example 1 is followed for preparing the technetium complex according to table 1 from the 2-methoxy tert-butyl amine isolated in the preceding example.

The characteristics of the complex obtained are given in table 1.

EXAMPLES 11 AND 12

The technetium complexes according to table 1 are prepared, following the operating procedure of example 1, but starting with tetrahydro-furfuryl amine, which is treated by bromomethane in example 11 and by bromoethane in example 12.

The characteristics of the complexes obtained are given in table 1.

EXAMPLE 13

The complex mentioned in table 1 is prepared by following the same operating procedure as in example 1, starting with N-ethyl. N-2-(2-methoxyethoxy)-ethyl amine prepared in the following way.

Dropwise addition takes place of 0.2 mole of 1-bromo-2-(2-methoxyethoxy)-ethane (Aldrich) to an aqueous ethyl amine solution. Refluxing takes place for 6 hours. The solution is filtered and is extracted with ether. The organic phase is distilled.

The characteristics of the complex obtained are given in table 1.

EXAMPLE 14

The complex according to table 1 is prepared by following the same operating procedure as in example 1, starting with the ligand sodium-N, N-bis(2,2-dimethoxyethyl)-dithiocarbamate, which is prepared from N,N-bis(2 2-dimethoxyethyl)-amine obtained in the following way.

0.2 mole of dimethyl acetal aminoacetaldehyde (Aldrich) is dissolved in 100 ml of water containing 0.3 mole of NaOH. Dropwise addition takes place of 0.2 mole of dimethyl acetal bromoacetaldehyde (Aldrich). The solution is refluxed for one night. The aqueous phase is extracted with 200 ml of diethyl ether. The organic phase is washed three times with 20 ml of 1N NaOH in water in order to eliminate the primary amine which has not reacted. The organic phase is dried on sodium sulphate and the secondary amine is distilled:

E=70° C. under 2 mm Hg.

NNIR analysis is deuterium DMSO of the ligand obtained

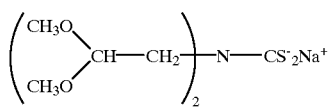

gives the following results:

$CH_3O$: singlet 3.4 ppm

CH: triplet 4.9 ppm $CH_2$: doublet 4.1 ppm

The characteristics of the complex obtained are given in table 1.

EXAMPLES 15 TO 24

The operating procedure of the preceding examples is followed for preparing the complexes indicated in table 1, starting with the amines and halides corresponding to the ligands of the complex.

The characteristics of the complexes obtained are given in table 1.

EXAMPLE 25

The biological properties of the complexes obtained in examples 1 to 24 are evaluated by determining the cardiac retention in baboons weighing between 9 and 12 kg.

To this end, injection takes place of 0.5 ml of solution of the final complex corresponding to an activity of 74 MBQ. The animal is anaesthetised by a ketamine/valium mixture and placed under a gamma camera. The retention of the radioactivity by the heart and the surrounding organs (lungs, liver) is determined by a dynamic acquisition for 60 minutes following the injection. Determination takes place of areas of interest for each organ and the retention values are calculated, being expressed in counts per minute per pixel (surface unit) and per mCi (cpm.pix$^{-1}$mCi$^{-1}$). These values are corrected by the radioactive decay of the radioelement. Blood samples are taken during the examination and their activity counted, which makes it possible to calculate the radioactivity percentage present in the total blood (circulating activity).

The cardiac retention values, the heart/lungs and heart/liver ratios giving an indication of the scintigraphic contrast and the blood activity values obtained with the complexes of examples 1 to 24 are given in the following table 2.

This table gives for comparison purposes the results obtained under the same conditions with the cardiac tracer MIBI marketed by Dupont and with the prior art complies $^{99m}$TcN-NOET, which is nitride-bis [N-ethoxy,N-ethyl-dithiocarbamate]$^{99m}$Tc(V) and which complies with formula (I), in which $L^1$ and $L^2$ are:

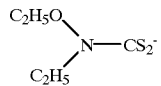

The results of table 2 demonstrate that most of the complexes have a cardiac retention superior to that of MIBI and equivalent to that of TcN NOET.

However, the cardiac activity decreases in time, which leads to a drop in the heart/lung and heart/liver scintigraphic ratios.

The blood clearance is rapid for most of the tested complexes.

The ideal period for cardiac imaging with this type of complex is consequently between 5 and 30 minutes after the injection.

The rapid elimination of the myocardium can permit a second injection 1 hour after the first, because the residual hepatic activity is no longer disturbing, because it is concentrated in the gall bladder with this type of tracer.

Thus, the scintigraphic images show that one hour after the injection, the residual hepatic activity is concentrated in the gall bladder, except for the complex of example 24.

Conversely, the scintigraphic images taken of the baboon with compounds of examples 11 and 17 of WO-A-90/06137 revealed that the residual hepatic activity was maintained throughout the liver.

It is also pointed out that the complexes which are of greatest interest are those of examples 1, 2, 3, 7, 12, 14, 15 and 18, the best being those of examples 1, 2, 3, 14, 15 and 18.

TABLE 1

| EXAMPLE | COMPLEX | $L^1 = L^2$ | | Rf | PRC |
|---|---|---|---|---|---|
| 1 | nitrido-bis[N-ethyl, N-(RS-2-methoxy isopropyl)dithiocarbamato]$^{99m}$TC(V) | $CH_3O\!-\!CH_2\!-\!\underset{\underset{CH_3}{\mid}}{CH}\!-\!\underset{\underset{C_2H_5}{\mid}}{N}\!-\!CS_2$ | (R, S) | 0.52 | $\geq$96% |
| 2 | nitrido-bis[N-ethyl, N-(R-2-methoxy isopropyl)dithiocarbamato]$^{99m}$Tc(V) | $CH_3O\!-\!CH_2\!-\!\underset{\underset{CH_3}{\mid}}{CH}\!-\!\underset{\underset{C_2H_5}{\mid}}{N}\!-\!CS_2$ | (R) | 0.52 | $\geq$97% |
| 3 | nitrido-bis[N-ethyl, N-(S-2-methoxy isopropyl)dithiocarbamato]$^{99m}$Tc(V) | $CH_3O\!-\!CH_2\!-\!\underset{\underset{CH_3}{\mid}}{CH}\!-\!\underset{\underset{C_2H_5}{\mid}}{N}\!-\!CS_2$ | (S) | 0.52 | $\geq$95% |
| 4 | nitrido-bis[N-methyl, N-(RS-2-methoxy isopropyl)dithiocarbamato]$^{99m}$Tc(V) | $CH_3O\!-\!CH_2\!-\!\underset{\underset{CH_3}{\mid}}{CH}\!-\!\underset{\underset{CH_3}{\mid}}{N}\!-\!CS_2$ | (R,S) | 0.61 | $\geq$96% |

TABLE 1(a)

| EXAMPLE | COMPLEX | $L^1 = L^2$ | | Rf | PRC |
|---|---|---|---|---|---|
| 5 | nitrido-bis[N-propyl, N-(R,S-2-methoxy isopropyl)dithiocarbamato]$^{99m}$Tc(V) | $CH_3O\!-\!CH_2\!-\!\underset{\underset{CH_3}{\mid}}{CH}\!-\!\underset{\underset{C_3H_7}{\mid}}{N}\!-\!CS_2$ | (R, S) | 0.39 | $\geq$97% |
| 6 | nitrido-bis[N-isopropyl, N-(R,S-2-methoxy isopropyl)dithiocarbamato]$^{99m}$Tc(V) | $CH_3O\!-\!CH_2\!-\!\underset{\underset{CH_3}{\mid}}{CH}\!-\!\underset{\underset{i\text{-}C_3H_7}{\mid}}{N}\!-\!CS_2$ | (R, S) | 0.35 | $\geq$92% |

TABLE 1(a)-continued

| EXAMPLE | COMPLEX | L¹ = L² | Rf | PRC |
|---|---|---|---|---|
| 7 | nitrido-bis[N-ethyl, N-(R,S-2-methoxy propyl)dithiocarbamato]$^{99m}$Tc(V) | $CH_3O-\overset{\bullet(R,S)}{\underset{CH_3}{CH}}-CH_2-\underset{C_2H_5}{N}-CS_2$ | 0.45 | ≧98% |
| 8 | nitrido-bis[N-ethyl, N-(R,S-1-methoxy methyl) propyl dithiocarbamato]$^{99m}$Tc(V) | $CH_3O-CH_2-\overset{\bullet(R,S)}{\underset{C_2H_5}{CH}}-\underset{C_2H_5}{N}-CS_2$ | 0.46 | ≧98% |

TABLE 1(b)

| EXAMPLE | COMPLEX | L¹ = L² | Rf | PRC |
|---|---|---|---|---|
| 9 | nitrido-bis[N-ethyl,N-(2-methoxy isobutyl) dithiocarbamato]$^{99m}$Tc(V) | $CH_3O-\overset{CH_3}{\underset{CH_3}{C}}-CH_2-\underset{C_2H_5}{N}-CS_2$ | 0.43 | ≧92% |
| 10 | nitrido-bis[N-ethyl,N-(2-methoxy tertbutyl) dithiocarbamato]$^{99m}$Tc(V) | $CH_3O-CH_2-\overset{CH_3}{\underset{CH_3}{C}}-\underset{C_2H_5}{N}-CS_2$ | 0.50 | ≧95% |
| 11 | nitrido-bis[N-methyl,N(R,S,-1-tetrahydrofurfuryl) dithiocarbamato]$^{99m}$Tc(V) | (tetrahydrofuran ring)*–CH$_2$–N(CH$_3$)–CS$_2$ | 0.70 | ≧95% |

TABLE 1(c)

| EXAMPLE | COMPLEX | L¹ = L² | Rf | PRC |
|---|---|---|---|---|
| 12 | nitrido-bis[N-ethyl, N(R,S 1-tetrahydrofurfuryl) dithiocarbamato]$^{99m}$Tc(v) | (tetrahydrofuran ring)*–CH$_2$–N(C$_2$H$_5$)–CS$_2$ | 0.61 | ≧97% |
| 13 | nitrido-bis[N-ethyl, N-2(2-methoxy ethoxy)ethyl) dithiocarbamato]$^{99m}$Tc(V) | $CH_3O-CH_2-CH_2-O-CH_2-CH_2-\underset{C_2H_5}{N}-CS_2$ | 0.71 | ≧98% |
| 14 | nitrido-bis[N-N-bis(2,2-dimethoxy ethyl) dithiocarbamato]$^{99m}$Tc(V) | $\left(\underset{CH_3O}{\overset{CH_3O}{\diagdown}}CH-CH_2-\right)_2 N-CS_2$ | 0.45 | ≧96% |

TABLE 1(d)

| EXAMPLE | COMPLEX | L¹ = L² | Rf | PRC |
|---|---|---|---|---|
| 15 | nitrido-bis[N-(2,2-dimethoxyethyl)N-(3,3-diemthoxypropyl)dithiocarbamato]$^{99m}$Tc(V) | | 0.45 | ≧97% |
| 16 | nitrido-bis[N-(2,2-dimethoxyethyl)N-(2,2-dimethoxypropyl)dithiocarbamato]$^{99m}$Tc(V) | | 0.40 | ≧94% |
| 17 | nitrido-bis[N-(2,2-dimethoxyethyl)N-(2,2-diethoxyethyl)dithiocarbamato]$^{99m}$Tc(V) | | 0.33 | ≧95% |

TABLE 1(e)

| EXAMPLE | COMPLEX | L¹ = L² | Rf | PRC |
|---|---|---|---|---|
| 18 | nitrido-bis[N-(2,2-dimethoxy ethyl)N-(ethyl)dithiocarbamato]$^{99m}$Tc(V) | | 0.47 | ≧96% |
| 19 | nitrido-bis[N-(2,2-dimethoxy ethyl)N-(isopropyl)dithiocarbamato]$^{99m}$Tc(V) | | 0.35 | ≧95% |
| 20 | nitrido-bis[N-(2,2-dimethoxy ethyl)N-(R,S-2-methoxy isopropyl)dithiocarbamato]$^{99m}$Tc(V) | | 0.47 | ≧92% |

TABLE 1(f)

| EXAMPLE | COMPLEX | $L^1 = L^2$ | Rf | PRC |
|---|---|---|---|---|
| 21 | nitrido-bis[N-N-bis(2,2-diethoxyethyl) dithiocarbamato]$^{99m}$Tc(V) | $\left(\begin{array}{c}C_2H_5O\\ \\C_2H_5O\end{array}CH-CH_2\right)_2 N-CS_2$ | 0.13 | ≧98% |
| 22 | nitrido-bis[N-(2,2-diethoxyethyl, N(2,2-diethylene acetal) ethyl)dithiocarbamato]$^{99m}$Tc(V) | (structure with C₂H₅O groups and dioxolane ring) | 0.37 | ≧95% |
| 23 | nitrido-bis[N-N-bis(2,2-diethylene acetal ethyl)dithiocarbamato]$^{99m}$Tc(V) | (bis-dioxolane structure) N—CS₂ | 0.55 | ≧95% |
| 24 | nitrido-bis[8-aza-1,4-dioxaspiro(4,5) decane dithiocarbamato]$^{99m}$Tc(V) | (spiro dioxolane-piperidine)N—CS₂ | 0.52 | ≧93% |

TABLE 2

| | $^{99m}$Tc Complex | | | | | | | | | | | | | | | | | | | |
|---|---|---|---|---|---|---|---|---|---|---|---|---|---|---|---|---|---|---|---|---|
| Time after | Cardiac retention cpm · pix$^{-1}$ mCi$^{-1}$ | | | | | Heart/lungs | | | | | Heart/liver | | | | | Blood activity (% injected dose) | | | | |
| injection (min) | 5 | 10 | 15 | 30 | 60 | 5 | 10 | 15 | 30 | 60 | 5 | 10 | 15 | 30 | 60 | 5 | 10 | 15 | 30 | 60 |
| $^{99m}$Tc MIBI | 21 | 21 | 21 | 18 | 17 | 3.1 | 3.1 | 3.1 | 2.7 | 3 | 0.55 | 0.56 | 0.55 | 0.66 | 0.75 | 15 | 1.7 | 0.8 | 0.7 | 0.8 |
| $^{99m}$TcN NOET | 39 | 37 | 35 | 35 | 34 | 1.1 | 1.3 | 1.4 | 1.8 | 2.3 | 1.4 | 1.2 | 1 | 0.9 | 0.8 | 2.4 | 2 | 1.7 | 1.6 | 1.9 |
| EXAMPLE 1 | 44 | 42 | 40 | 33 | 24 | 3.9 | 4.3 | 4.5 | 3.9 | 3.2 | 1 | 0.8 | 0.6 | 0.3 | 0.3 | 8 | — | 3 | 2 | 1.5 |
| EXAMPLE 2 | 31 | 27 | 26 | 24 | 22 | 2.7 | 2.9 | 2.7 | 2.7 | 2.5 | 0.8 | 0.6 | 0.6 | 0.5 | 0.4 | — | 5.2 | 3.2 | 2.9 | — |
| EXAMPLE 3 | 30 | 21 | 17 | 12 | 11 | 2.6 | 2.2 | 1.9 | 1.4 | 1.4 | 0.5 | 0.3 | 0.2 | 0.2 | 0.1 | 4.8 | — | 1.9 | 1.3 | 1.1 |
| EXAMPLE 4 | 35 | 22 | 18 | 14 | 12 | 5 | 3.1 | 2.6 | 2.2 | 2 | 0.6 | 0.3 | 0.3 | 0.2 | 0.2 | — | 4.6 | 4.6 | 2.4 | 1.8 |
| EXAMPLE 5 | 45 | 38 | 35 | 21 | 12 | 3.7 | 3.6 | 3.6 | 2.6 | 1.8 | 0.6 | 0.5 | 0.4 | 0.2 | 0.1 | 6.7 | 3.9 | — | 3.6 | |

TABLE 2(a)

| | $^{99m}$Tc Complex | | | | | | | | | | | | | | | | | | | |
|---|---|---|---|---|---|---|---|---|---|---|---|---|---|---|---|---|---|---|---|---|
| Time after | Cardiac retention cpm · pix$^{-1}$ mCi$^{-1}$ | | | | | Heart/lungs | | | | | Heart/liver | | | | | Blood activity (% injected dose) | | | | |
| injection (min) | 5 | 10 | 15 | 30 | 60 | 5 | 10 | 15 | 30 | 60 | 5 | 10 | 15 | 30 | 60 | 5 | 10 | 15 | 30 | 60 |
| EXAMPLE 6 | 32 | 27 | 25 | 18 | 14 | 2.9 | 2.9 | 2.7 | 2.1 | 1.8 | 0.4 | 0.3 | 0.2 | 0.2 | 0.1 | 11 | 6.5 | 5.1 | 3.7 | |
| EXAMPLE 7 | 51 | 41 | 38 | 28 | 22 | 4.1 | 4.3 | 4.2 | 3.4 | 2.9 | 0.8 | 0.6 | 0.5 | 0.3 | 0.2 | 4.4 | 3.5 | 2.8 | 2 | 1.7 |
| EXAMPLE 8 | 36 | 32 | 24 | 16 | 11 | 3.3 | 3.5 | 3.1 | 2.4 | 1.8 | 0.6 | 0.5 | 0.3 | 0.2 | 0.2 | 8.5 | | 5 | 2.8 | 2.1 |
| EXAMPLE 9 | 26 | 21 | 16 | 13 | 12 | 3 | 2.9 | 2.2 | 2 | 1.7 | 0.4 | 0.3 | 0.2 | 0.2 | 0.2 | 5.9 | — | 3.6 | 2.4 | 1.5 |
| EXAMPLE 10 | 31 | 25 | 23 | 19 | 14 | 3.2 | 3.1 | 3 | 2.8 | 2.2 | 0.5 | 0.4 | 0.3 | 0.2 | 0.2 | 9.4 | — | 7.1 | 4.9 | — |
| EXAMPLE 11 | 41 | 26 | 21 | 14 | 11 | 4.5 | 3.2 | 2.7 | 1.9 | 1.7 | 0.7 | 0.4 | 0.3 | 0.2 | 0.1 | — | 5.3 | | | |
| EXAMPLE 12 | 35 | 28 | 25 | 16 | 11 | 3.1 | 2.9 | 2.7 | 1.9 | 1.7 | 0.6 | 0.4 | 0.4 | 0.2 | 0.1 | 4.3 | | 2.5 | 1.5 | 1.3 |

TABLE 2(b)

| | ⁹⁹ᵐTc Complex | | | | | | | | | | | | | | | | | | | |
|---|---|---|---|---|---|---|---|---|---|---|---|---|---|---|---|---|---|---|---|---|
| Temps après | Cardiac retention cpm · pix⁻¹ mCi⁻¹ | | | | | Heart/lungs | | | | | Heart/liver | | | | | Blood activity (% injected dose) | | | | |
| injection (min) | 5 | 10 | 15 | 30 | 60 | 5 | 10 | 15 | 30 | 60 | 5 | 10 | 15 | 30 | 60 | 5 | 10 | 15 | 30 | 60 |
| EXAMPLE 13 | 37 | 35 | 34 | 22 | 14 | 2.9 | 3.3 | 3.3 | 2.5 | 1.9 | 0.6 | 0.5 | 0.4 | 0.2 | 0.1 | 4.5 | — | 2.4 | 2.1 | 1.6 |
| EXAMPLE 14 | 46 | 41 | 34 | 20 | 11 | 4.9 | 5 | 4.2 | 2.9 | 2 | 0.9 | 0.6 | 0.5 | 0.3 | 0.2 | 6.8 | — | 5 | 4.3 | 2.7 |
| EXAMPLE 15 | 49 | 44 | 39 | 25 | 15 | 4.1 | 4.4 | 4.4 | 3.2 | 2.2 | 0.8 | 0.6 | 0.5 | 0.3 | 0.2 | 12 | 5 | 4.5 | | |
| EXAMPLE 16 | 44 | 37 | 33 | 21 | 12 | 3.3 | 3.3 | 3 | 2.2 | 1.6 | 0.8 | 0.6 | 0. | 0.2 | 0.1 | 3.9 | 4.2 | 4.3 | 4 | 2.7 |
| EXAMPLE 17 | 29 | 27 | 26 | 23 | 19 | 3 | 3.1 | 3.2 | 3.1 | 2.7 | 0.5 | 0.4 | 0.4 | 0.3 | 0.3 | | 4.5 | 2.4 | 2.1 | |
| EXAMPLE 18 | 40 | 34 | 28 | 19 | 13 | 3.7 | 3.5 | 3 | 2.1 | 1.4 | 0.6 | 0.5 | 0.4 | 0.2 | 0.1 | 8.6 | 4.2 | 3.8 | | 2.5 |
| EXAMPLE 19 | 31 | 28 | 27 | 21 | 15 | 2.7 | 2.8 | 2.8 | 2.5 | 1.9 | 0.4 | 0.4 | 0.3 | 0.3 | 0.2 | 7.6 | | 5.2 | 5.6 | 4.5 |

TABLE 2(c)

| | ⁹⁹ᵐTc Complex | | | | | | | | | | | | | | | | | | | |
|---|---|---|---|---|---|---|---|---|---|---|---|---|---|---|---|---|---|---|---|---|
| Time after | Cardiac retention cpm · pix⁻¹ mCi⁻¹ | | | | | Heart/lungs | | | | | Heart/liver | | | | | Blood activity (% injected dose) | | | | |
| injection (min) | 5 | 10 | 15 | 30 | 60 | 5 | 10 | 15 | 30 | 60 | 5 | 10 | 15 | 30 | 60 | 5 | 10 | 15 | 30 | 60 |
| EXAMPLE 20 | 42 | 35 | 2.9 | 16 | 13 | 3.2 | 3 | 2.7 | 1.8 | 1.5 | 0.9 | 0.6 | 0.4 | 0.2 | 0.1 | 10.1 | 8.9 | 8.7 | 8.3 | 7.6 |
| EXAMPLE 21 | 26 | 18 | 15 | 13 | 9 | 2 | 1.7 | 1.6 | 1.4 | 1.3 | 0.5 | 0.3 | 0.3 | 0.2 | 0.2 | 23.2 | 12.5 | | 4.3 | |
| EXAMPLE 22 | 36 | 25 | 21 | 15 | 10 | 3.3 | 3 | 2.6 | 2.1 | 1.6 | 0.6 | 0.4 | 0.3 | 0.2 | 0.2 | 5.1 | 3.9 | | 3 | |
| EXAMPLE 23 | 36 | 24 | 19 | 13 | 9 | 3.6 | 2.6 | 2 | 1.5 | 1.2 | 0.9 | 0.5 | 0.3 | 0.2 | 0.3 | 9.2 | 3.5 | 2.8 | | |
| EXAMPLE 24 | 23 | 16 | 14 | 13 | 12 | 2.4 | 1.7 | 1.5 | 1.4 | 1.4 | 0.3 | 0.3 | 0.2 | 0.2 | 0.2 | 4.6 | — | 3.3 | 2.5 | — |

We claim:

1. A radiopharmaceutical product, comprising a complex of a transition metal of the formula:

$$(M\equiv N)L^1 L^2 \quad (I)$$

in which M is a transition metal, and $L^1$ and $L^2$, which can be the same or different, comply with the formula:

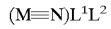

(II)

in which R and R', which are the same or different, represent:

an alkyl group, a group of formula:

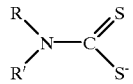

(III)

in which:

$R^1$ is an alkyl group, $R^2$ is an alkyl group or an alkoxy group, or $R^1$ and $R^2$ form together the group —$CH_2CH_2O$—, $R^3$ is a hydrogen atom or an alkyl group and n is equal to 0, 1, 2 or 3, a group of formula:

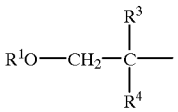

(IV)

in which $R^1$ and $R^3$ are as defined hereinbefore and $R^4$ is an alkyl group, the group of formula:

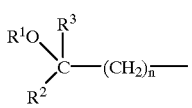

(V)

a group of formula:

$R^1O(CH_2CH_2O)_p CH_2CH_2$— (VI)

in which $R^1$ is as defined hereinbefore and p is equal to 1 or 2, or in which R and R' together with the nitrogen atom to which they are linked, form the group of formula:

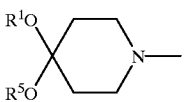

(VII)

in which $R^1$ and $R^5$ are identical or different alkyl groups, or in which $R^1$ and $R^5$ form together —$CH_2$—$CH_2$—, provided that both R and R' do not represent an alkyl group.

2. A radiopharmaceutical product according to claim 1, wherein M represents an isotope of technetium or rhenium.

3. A radiopharmaceutical product according to claim 2, wherein the isotope of technetium is Tc-99m.

4. A radiopharmaceutical product according to claim 2, wherein the isotope of rhenium is Re-186 or Re-188.

5. A radiopharmaceutical product according to claim 1, wherein $L^1$ and $L^2$ are identical.

6. A radiopharmaceutical product according to claim 1, wherein at least one of the $L^1$ and $L^2$ complies with the formula (II) in which:

R and/or R' represent a group of formula:

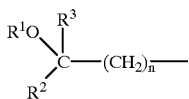

(III)

in which $R^1$ represents an alkyl group, $R^2$ represents an alkoxy group, $R^3$ represents a hydrogen atom or an alkyl group, and n is equal to 0, 1, 2 or 3.

7. A radiopharmaceutical product according to claim 1, wherein at least one of the L1 and L2 complies with the formula (II) in which:

R and/or R' represent a group of formula:

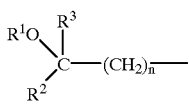

(III)

in which $R^1$, $R^2$ and $R^3$ are identical or different alkyl groups.

8. A radiopharmaceutical product according to claim 1, wherein the complex is chosen from within the group consisting of:

nitrido-bis[N-ethyl-N(R,S-methoxypropyl) dithiocarbamato]$^{99m}$Tc(V), nitrido-bis[N-ethyl-N(2-methoxyisobutyl) dithiocarbamato]$^{99m}$Tc(V), nitrido-bis[N-,N-bis-2,2-dimethoxyethyl) dithiocarbamato]$^{99m}$Tc(V), nitrido-bis[N-(2,2-dimethoxyethyl), N-(3,3-dimethoxypropyl)dithiocarbamato]$^{99m}$Tc(V), nitrido-bis[N-(2,2-dimethoxyethyl), N-(2,2-dimethoxypropyl) dithiocarbamato]$^{99m}$Tc(V), nitrido-bis[N-(2,2-dimethoxyethyl), N-(2,2-diethoxyethyl) dithiocarbamato]$^{99m}$Tc(V), nitrido-bis-[N-(2,2-dimethoxyethyl), N-ethyl dithiocarbamato]$^{99m}$Tc(V), nitrido-bis [N-(2,2-dimethoxyethyl), N-isopropyl dithiocarbamato]$^{99m}$Tc(V), nitrido-bis[N,N-bis(2,2-diethoxyethyl), dithiocarbamato] $^{99m}$Tc(V), nitrido-bis[N-(2,2-diethoxyethyl), N(2,2 (diethyleneacetal)ethyl) dithiocarbamato]$^{99m}$Tc(V), nitrido-bis-[N,N-bis(2,2(diethyleneacetal)ethyl) dithiocarbamato]$^{99m}$Tc(V).

9. A radiopharmaceutical product according to any claim 1, wherein at least one of the L1 and L2 complies with formula (II) in which:

R and/or R' comply with the formula (IV):

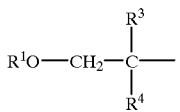

(IV)

in which $R^1$ represents an alkyl group, $R^3$ represents a hydrogen atom and $R^4$ represents an alkyl group.

10. A radiopharmaceutical product according to claim 9, wherein the complex is chosen in the group consisting of:

nitrido-bis[N-ethyl, N-(R-S-2 methoxyisopropyl) dithiocarbamato]$^{99m}$Tc(V), nitrido-bis[(N-ethyl, N-(R-2-methoxyisopropyl) dithiocarbamato]$^{99m}$Tc(V), nitrido-bis[(N-ethyl, N(S-2-methoxyisopropyl) dithiocarbamato]$^{99m}$Tc(V), nitrido-bis[(N-methyl, N(R,S)-2-methoxyisopropyl) dithiocarbamato]$^{99m}$Tc(V), nitrido-bis[(N-propyl, N-(R,S)2-methoxyisopropyl) dithiocarbamato]$^{99m}$Tc(V), nitrido-bis[N-isopropyl, N(R,S)-2-methoxyisopropyl) dithiocarbamato]$^{99m}$Tc(V), nitrido-bis[(N-ethyl, N(R,S)-1-methoxymethyl)propyl) dithiocarbamato]$^{99m}$Tc(V), nitrido-bis[N-ethyl, N-(2-methoxy tert-butyl) dithiocarbamato]$^{99m}$Tc(V), nitrido-bis[N-(2,2-dimethoxyethyl), N(R,S)2-methoxyisopropyl) dithiocarbamato]$^{99m}$Tc(V).

11. A radiopharmaceutical product according to claim 1, wherein at least one of the $L^1$ and $L^2$ complies with formula (II) in which:

R and/or $R^1$ represent the group of formula:

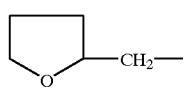

(V)

12. A radiopharmaceutical product according to claim 11, wherein the complex is chosen from among:

nitrido-bis[(N-methyl, N-(R,S) 1-tertrahydrofurfuryl) dithiocarbamato]$^{99m}$Tc(V), and nitrido-bis[(N-ethyl N-(R,S) 1-tetrahydrofurfuryl) dithiocarbamato]$^{99m}$Tc(V).

13. A radiopharmaceutical product according to claim 1, wherein the complex is nitrido-bis[(N-ethyl, N-2(2-methoxyethoxy) ethyl) dithiocarbamato]$^{99m}$Tc(V) or nitrido-bis[8-aza-1,4-dioxaspiro (4,5)-decane dithiocarbamato]$^{99m}$Tc(V).

14. A process for the preparation of a radiopharmaceutical product according to claim 1, comprising reacting in solution an oxygen compound of the transition metal M, with 1) a nitrogen ligand constituted either by a pharmaceutically acceptable metal or ammonium nitride, or by a nitrogen compound having a N—N unit, in which the Ns are connected to hydrogen atoms and/or monovalent organic groups via a carbon atom or a S atom, or in which one of the Ns is connected to the carbon atom of a divalent organic group via a double bond and the other N is connected to hydrogen atoms and/or monovalent organic groups via a carbon atom;

2) a reducing agent constituted either by a pharmaceutically acceptable metal or ammonium dithionite, or by tin II present in ionic form in the solution; and 3) a compound complying with the formula:

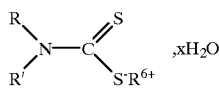
(VIII)

in which R and R' have the meanings given hereinbefore, $R^6$ is an alkali metal, $H^+$ or $NH^{4+}$ ion, and x is equal to 0 or an integer from 1 to 5.

15. The process according to claim 14, wherein the nitrogen ligand is succinyl dihydrazide and the reducing agent stannous chloride dihydrate.

16. A kit for the preparation of the radiopharmaceutical product according to claim 1, comprising:
  a first bottle containing a tin salt and a complexing agent able to keep the tin in ionic form,
  a second bottle containing a nitrogen ligand and
  a third bottle containing a compound complying with the formula:

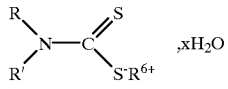
(VIII)

in which R and R' have the meanings given in claim 1, $R^6$ is an alkali metal, $H^+$ or $NH^{4+}$ ion, and x is equal to 0 or an integer from 1 to 5.

17. A kit for the preparation of the radiopharmaceutical product according to claim 1, comprising:
  a first bottle containing a tin salt, a nitrogen ligand and a complexing agent able to keep the tin in ionic form and
  a second bottle containing a compound of formula:

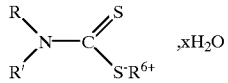
(VIII)

in which R and R' have the meanings given in claim 1, $R^6$ is an alkali metal, $H^+$ or $NH^{4+}$ ion, and x is equal to 0 or an integer from 1 to 5.

18. The kit according to claim 16, wherein the compound of formula (VIII) is selected from the group consisting of:
  sodium-(N-ethyl, N-(R,S)-2-methoxyisopropyl)-dithiocarbamate,
  sodium-(N-ethyl, N(R)-2-methoxyisopropyl)-dithiocarbamate,
  sodium-(N-ethyl, N-(S)-2-methoxyisopropyl)-dithiocarbamate,
  sodium-[N,N-bis(2,2-dimethoxyethyl)]-dithiocarbamate,
  sodium-[N-(2,2-dimethoxyethyl), N-(3,3-dimethoxypropyl)]-dithiocarbamate,
  sodium-[N](2,2-dimethoxyethyl), N-ethyl)]-dithiocarbamate.

19. The kit according to claim 16, characterized in that the tin salt is stannous chloride, the complexing agent is 1,2-diaminopropane-N,N,N',N'-tetraacetic acid or a salt thereof and the nitrogen ligand is succinyl dihydrazide.

20. A radiopharmaceutical product according to any one of the claims 1 to 13 for scintigraphy of the myocardium.

21. The kit according to claim 17, wherein the compound of formula (VIII) is selected from the group consisting of
  sodium-(N-ethyl, N-(R,S)-2-methoxyisopropyl)-dithiocarbamate,
  sodium-(N-ethyl, N-(R)-2-methoxyisopropyl)-dithiocarbamate,
  sodium-(N-ethyl, N-(S)-2-methoxyisopropyl)-dithiocarbamate,
  sodium- [N,N-bis(2,2-dimethoxyethyl)]-dithiocarbamate,
  sodium-[N-(2,2-dimethoxyethyl), N-(3,3-dimethoxypropyl)]-dithiocarbamate, and
  sodium-[N-(2,2-dimethoxyethyl), N-ethyl)]-dithiocarbamate.

22. The kit according to claim 17, wherein the tin salt is stannous chloride, the complexing agent is 1,2-diaminopropane-N,N,N',N'-tetraacetic acid or a salt thereof, and the nitrogen is succinyl dihydrazide.

* * * * *